(12) United States Patent
Xu et al.

(10) Patent No.: US 6,440,202 B1
(45) Date of Patent: Aug. 27, 2002

(54) PYRAZOLATE COPPER COMPLEXES, AND MOCVD OF COPPER USING SAME

(75) Inventors: Chongying Xu, New Milford; Thomas H. Baum, New Fairfield, both of CT (US); Ziyun Wang, Austin, TX (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 10/015,359

(22) Filed: Dec. 13, 2001

Related U.S. Application Data

(63) Continuation of application No. 09/524,063, filed on Mar. 13, 2000.

(51) Int. Cl.[7] ............................................. C23C 16/18
(52) U.S. Cl. ...................................... 106/1.18; 106/1.26
(58) Field of Search ............................... 106/1.18, 1.26

(56) References Cited

U.S. PATENT DOCUMENTS

| | | | |
|---|---|---|---|
| 5,085,731 A | 2/1992 | Norman et al. | 216/105 |
| 5,098,516 A | 3/1992 | Norman et al. | 216/78 |
| 5,144,049 A | 9/1992 | Norman et al. | 556/12 |
| 5,204,314 A | 4/1993 | Kirlin | 505/447 |
| 5,225,561 A | 7/1993 | Kirlin et al. | 546/256 |
| 5,280,012 A | 1/1994 | Kirlin et al. | 505/447 |
| 5,322,712 A | 6/1994 | Norman et al. | 427/250 |
| 5,362,328 A | 11/1994 | Gardiner et al. | 118/726 |
| 5,453,494 A | 9/1995 | Kirlin et al. | 534/15 |
| 5,536,323 A | 7/1996 | Kirlin et al. | 118/726 |
| 5,711,816 A | 1/1998 | Kirlin et al. | 118/726 |
| 5,820,664 A | 10/1998 | Gardiner et al. | 106/287.17 |
| 5,919,522 A | 7/1999 | Baum et al. | 427/248.1 |
| 6,110,529 A * | 8/2000 | Gardiner et al. | 427/250 |
| 6,337,148 B1 * | 1/2002 | Xu et al. | 427/252 |

FOREIGN PATENT DOCUMENTS

WO      WO 0168948 A1 * 9/2001

OTHER PUBLICATIONS

H.V. Rasika Dias, Sharon A. Polach, and Ziyun Wang, "Coinage Metal Complexes of 3,5–bis(trifluoromethyl)pyrazolate Ligand: Synthesis and Characterization of {[3,5–(CF3)2Pz]Cu}3 and {[3,5–(CF3)2Pz]Ag}3", Journal of Fluorine Chemistry 2000, 103, 163–169, No month available.

* cited by examiner

*Primary Examiner*—Helene Klemanski
(74) *Attorney, Agent, or Firm*—Oliver A. Zitzmann; Margaret Chappuis; Steven J. Hultquist

(57) ABSTRACT

Copper pyrazolate precursor compositions useful for the formation of copper in semiconductor integrated circuits, e.g., interconnect metallization in semiconductor device structures, as an adhesive seed layer for plating, for the deposition of a thin-film recording head and for circuitization of packaging components. The copper pyrazolate precursor compositions include fluorinated and non-fluorinated pyrazolate copper (I) complexes and their Lewis base adducts. Such precursors are usefully employed for liquid delivery chemical vapor deposition of copper or copper-containing material on a substrate.

9 Claims, 7 Drawing Sheets

PYRAZOLATE COPPER COMPLEXES, AND MOCVD OF COPPER USING SAME

This application is a Continuation of application Ser. No. 09/524,063, filed Mar. 13, 20000.

BACKGROUND OF THE INVENTION

1. Field Of The Invention

The present invention relates to copper precursor compositions and their synthesis, and to a method for production of copper circuits in microelectronic device structures, as for example in formation of metal interconnects for the manufacture of semiconductor integrated circuits, thin-film recording heads and packaging components, or otherwise for metallizing or forming copper-containing films on a substrate by metalorganic chemical vapor deposition (MOCVD) utilizing such precursor compositions. The precursor compositions of the invention are also usefully employed for forming seed layers of copper for subsequent electroless or electrochemical plating of copper and other metals.

2. Description of the Related Art

As a result of its low resistivity, low contact resistance, and ability to enhance device performance through the reduction of RC time delays, copper has emerged as a preferred metal for metallization of VLSI devices. Copper metallization has been adopted by many semiconductor device manufacturers for production of microelectronic chips, thin-film recording heads and packaging components.

Chemical vapor deposition (CVD) of copper provides uniform coverage for the metallization. Liquid CVD precursors and/or solid precursors dissolved into solvents or excess ligands enable direct injection and/or the liquid delivery of precursors into a CVD vaporizer unit. The accurate and precise delivery rate can be obtained through volumetric metering to achieve reproducibility during CVD metallization of a VLSI device.

Currently only a few liquid copper precursors are commercially available. These include (hfac)Cu(MHY), (hfac)Cu(3-hexyne), (hfac)Cu(DMCOD) and (hfac)Cu(VTMS), wherein hfac=1,1,1,5,5,5-hexafluoroacetylacetonato, MHY=2-methyl-1-hexen-3-yne, DMCOD=dimethylcyclooctadiene, and VTMS=vinyltrimethylsilane.

Various copper precursors useful for MOCVD of copper interconnects in semiconductor integrated circuits are described in U.S. Pat. Nos. 5,085,731; 5,098,516; 5,144,049; and 5,322,712; and the references cited in those patents. New and useful compositions and processes for the production of copper that improve on, or provide alternatives to, these known compositions would be highly desirable and embody a significant advance in the art.

With respect to the copper precursors that have come into use for copper MOCVD metallization, there are concerns associated with using (hfac)CuL precursors, where hfac=1,1,1,5,5,5-hexafluoroacetylacetonate and L=neutral Lewis base ligands. Copper metallization in integrated circuit manufacture typically utilizes a barrier layer between the copper layer and the underlying structure in order to prevent detrimental effects that may be caused by the interaction of a copper layer with other portions of the integrated circuit. A wide range of barrier materials is conventionally utilized, including materials comprising metals, metal nitrides, metal silicides, and metal silicon nitrides. Exemplary barrier materials include titanium nitride, titanium silicide, tantalum nitride, tantalum silicide, tantalum silicon nitrides, niobium nitrides, niobium silicon nitrides, tungsten nitride, and tungsten silicide. In instances where (hfac)CuL type precursors are used for copper metallization, interfacial layers are formed between the barrier layer and the copper layer. These interfacial layers cause the metallization to have poor adhesion and high contact resistivity.

The deficiencies of inferior adhesion and excessively high contact resistivity incident to formation of interfacial layers when using (hfac)CuL copper precursors has been attributed to the hfac ligand, which contains both oxygen and fluorine. To overcome such deficiencies, it would be a significant advance in the art to provide copper MOCVD precursors having a reduced oxy/fluoro content. It would be particularly advantageous to provide copper MOCVD precursors of an oxygen-free character.

It is accordingly an object of the present invention to provide a new class of anoxic (oxygen-free) copper precursors and formulations.

It is another object of the invention to provide methods of forming copper in the manufacturing of integrated circuits and other microelectronic device structures using such precursors and formulations.

It is a further object of the invention to provide metallization technology for forming interconnects and other device structures that overcome the shortcomings and limitations of the prior art, including improved adhesion, improved contact resistances, improved film resistivities and improved device integration.

It is another object of the invention to provide a method of metallizing or forming copper-containing films on a substrate by metalorganic chemical vapor deposition (MOCVD) utilizing such novel copper precursor compositions and formulations.

It is a further object of the invention to provide adherent thin-films for seeding electroless and/or electrochemical plating solutions and to overcome the shortcomings and limitations of the prior art, including improved adhesion, improved contact resistances, improved films resistivities, improved plating, improved conformality, improved manufacturing, and improved device integration.

Other objects and advantages of the present invention will be more fully apparent from the ensuing disclosure and appended claims.

SUMMARY OF THE INVENTION

The present invention relates generally to copper pyrazolate compositions, which are advantageously of an oxygen-free character, useful as source reagents for forming copper on substrates, and to methods of making and using such compositions.

In one aspect, the invention relates to a composition useful for the production of copper by chemical vapor deposition, comprising one or more pyrazolate copper (I) Lewis base adduct(s).

In a particular aspect, the invention relates to a copper precursor of the formula (RR'R")PzCuL, wherein (RR'R")Pz is a pyrazolyl moiety of the formula:

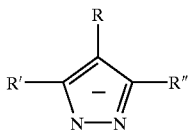

wherein R, R' and R" are independently the same as or different from one another and each of R, R' and R" is independently selected from H, $C_6$–$C_{10}$ aryl, $C_6$–$C_{10}$ fluoroaryl, $C_1$–$C_6$ alkyl, $C_1$–$C_6$ fluoroalkyl, $C_1$–$C_6$ perfluoroalkyl, and $C_3$–$C_6$ cycloalkyl, with the proviso that at least one R contains fluorine; and L is a neutral Lewis base ligand, such as a neutral Lewis base alkene, alkyne or diene.

A further aspect of the invention relates to pyrazolate copper (I) Lewis base adducts that are devoid of oxygen constituents therein.

Another aspect of the invention relates to specific copper precursor formulations useful for liquid delivery metalorganic chemical vapor deposition of copper, comprising:
(a) a precursor composition selected from the group consisting of:
  (i) pyrazolate copper (I) compounds; and
  (ii) pyrazolate copper (I) neutral Lewis base adducts; and
(b) a solvent composition for the precursor composition.

A further aspect of the invention relates to copper precursor formulations useful for liquid delivery metalorganic chemical vapor deposition of copper, comprising:
(a) a precursor composition selected from the group consisting of:
  (i) (RR'R")PzCu wherein: Pz is a pyrazolyl moiety and R, R' and R" are independently the same as or different from one another and each of R, R' and R" is independently selected from H, $C_6$–$C_{10}$ aryl, $C_6$–$C_{10}$ fluoroaryl, $C_1$–$C_6$ alkyl, $C_1$–$C_6$ fluoroalkyl, $C_1$–$C_6$ perfluoroalkyl, and $C_3$–$C_6$ cycloalkyl;
  (ii) (RR'R")PzCuL wherein: Pz is a pyrazolyl moiety and R, R' and R" are independently the same as or different from one another and each of R, R' and R" is independently selected from H, $C_6$–$C_{10}$ aryl, $C_6$–$C_{10}$ fluoroaryl, $C_1$–$C_6$ alkyl, $C_1$–$C_6$ fluoroalkyl, $C_1$–$C_6$ perfluoroalkyl, and $C_3$–$C_6$ cycloalkyl, with the proviso that at least one R contains fluorine; and L is a Lewis base ligand, such as an amine or a neutral Lewis base alkene, alkyne, or diene; and
(b) a solvent composition for the precursor composition.

A further aspect of the invention relates to pyrazolate copper (I) precursor formulations that are devoid of oxygen constituents therein.

Another aspect of the invention relates to specific copper precursors such as $[(CF_3)_2PzCu]_3$, $(CF_3)_2PzCu$(3-hexyne), and $(CF_3)_2PzCu$[bis(tms)acetylene], wherein Pz is a pyrazolyl moiety and tms is trimethylsilyl.

In further aspects, the invention variously relates to: a process useful for the production of copper, in which a composition of the above-described type is subjected to chemical vapor deposition; a process of forming a seed layer by liquid injection or direct vaporization of a composition of the above-described type; copper made by the process of subjecting to chemical vapor deposition a composition of such type; and integrated circuits made using such process.

A further aspect of the invention relates to a process for synthesizing a copper precursor, including reacting (RR'R") pyrazole starting material with a stoichiometric excess of $Cu_2O$, and recovering (R,R'R")pyrazolyl copper from the reaction, optionally followed by reacting the (R,R'R") pyrazolyl copper with a neutral Lewis base compound, to yield a (R,R'R")pyrazolyl copper Lewis base adduct. The Lewis base adducted pyrazolate copper complexes exhibit higher solubility in organic solvents. Such high solubility is particularly advantageous in making solution compositions using the solid complexes.

A still further aspect of the invention relates to a process for synthesizing a copper precursor, including reacting bis (trifluoromethyl)pyrazole with a stoichiometric excess of $Cu_2O$, and recovering bis(trifluoromethyl)pyrazolyl copper from the reaction, optionally followed by reacting the bis (trifluoromethyl)pyrazolyl copper with a neutral Lewis base compound, to yield a bis(trifluoromethyl)pyrazolyl copper Lewis base adduct. Another aspect of the invention relates to a process for synthesizing the (RR'R")pyrazolyl copper Lewis base adduct directly from the Lewis base in the presence of $Cu_2O$ and (RR'R")pyrazole starting material.

Yet another aspect of the invention relates to a method of depositing copper on a substrate, comprising volatilizing a copper precursor composition of the present invention, to form a precursor vapor and contacting the precursor vapor with the substrate under elevated temperature vapor decomposition conditions to deposit copper on the substrate.

The precursor compositions of the invention are useful for the manufacture of copper, including copper interconnects for integrated circuits, thin-film recording heads and/or packaging components.

Other aspects and features of the invention will be more fully apparent from the ensuing disclosure and appended claims.

DETAILED DESCRIPTION OF THE INVENTION AND PREFERRED EMBODIMENTS THEREOF

Figure 1:
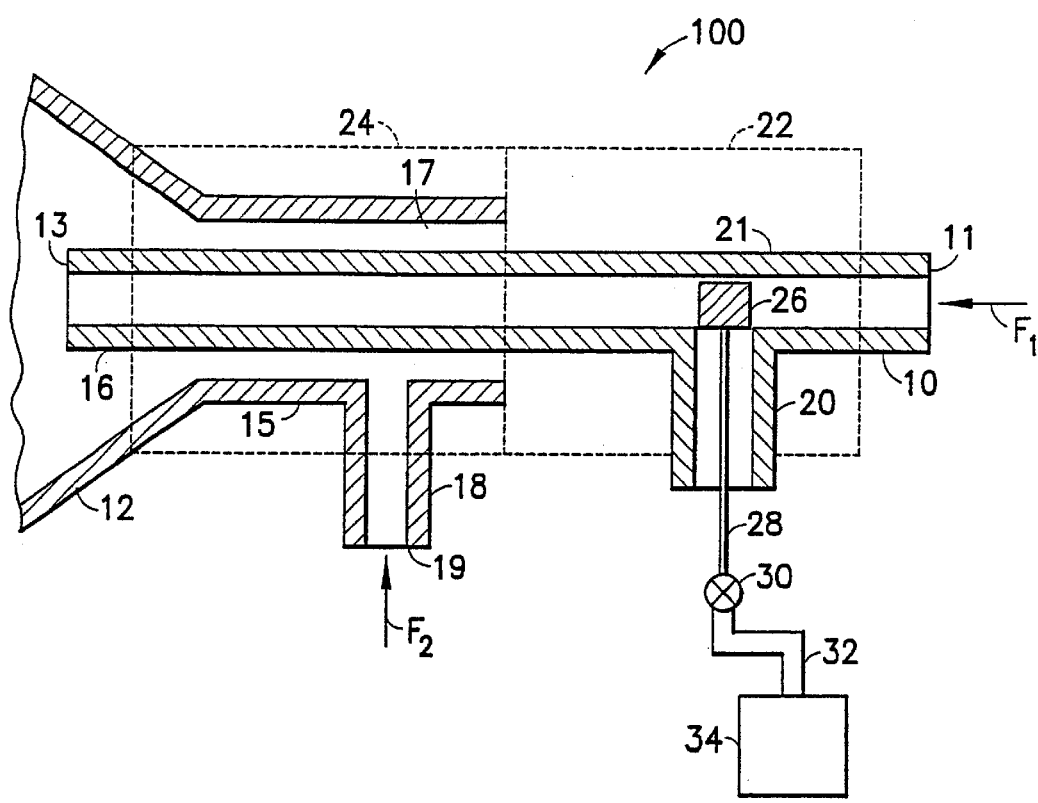
FIG. 1 is a schematic representation of a liquid delivery and vaporization system as may be used with a chemical vapor deposition (CVD) chamber for the deposition of copper-containing material on a substrate in accordance with the present invention.

The disclosures of the following United States patents and patent applications are hereby incorporated herein by reference in their entireties:

U.S. patent application Ser. No. 08/835,768 filed Apr. 8, 1997 in the names of Thomas H. Baum, et al., now U.S. Pat. No. 5,919,522;

U.S. patent application Ser. No. 08/484,654 filed Jun. 7, 1995 in the names of Robin A. Gardiner et al., now U.S. Pat. No. 6,110,529;

U.S. patent application Ser. No. 08/414,504 filed Mar. 31, 1995 in the names of Robin A. Gardiner et al., now U.S. Pat. No. 5,820,664;

U.S. application Ser. No. 08/280,143 filed Jul. 25, 1994, in the names of Peter S. Kirlin, et al., now U.S. Pat. No. 5,536,323;

U.S. patent application Ser. No. 07/927,134, filed Aug. 7, 1992 in the same names, now abandoned;

U.S. patent application Ser. No. 07/807,807, filed Dec. 13, 1991 in the names of Peter S. Kirlin, et al., now issued as U.S. Pat. No. 5,204,314;

U.S. application Ser. No. 08/181,800 filed Jan. 15, 1994 in the names of Peter S. Kirlin, et al., and issued as U.S. Pat. No. 5,453,494;

U.S. application Ser. No. 07/918,141 filed Jul. 22, 1992 in the names of Peter S. Kirlin, et al., and issued Jan. 18, 1994 as U.S. Pat. No. 5,280,012;

U.S. application Ser. No. 07/615,303 filed Nov. 19, 1990, now abandoned;

U.S. application Ser. No. 07/581,631 filed Sep. 12, 1990 in the names of Peter S. Kirlin, et al., and issued Jul. 6, 1993 as U.S. Pat. No. 5,225,561; and U.S. patent application Ser. No. 07/549,389 filed Jul. 6, 1990 in the names of Peter S. Kirlin, et al, now abandoned.

The oxygen-free pyrazolate copper compositions of the present invention are based on the discovery that 3,5-bis(trifluoromethyl)pyrazole may be used, instead of the (hfac)H ligand species that have been used to make prior art (hfac)CuL copper precursors, to produce useful precursors for MOCVD of copper.

The copper source reagents of the invention include pyrazolate copper (I) compounds, and pyrazolate copper (I) Lewis base adducts.

The pyrazolate copper (I) compounds of the invention include copper precursors of the formula [(RR'R")PzCu]$_3$ wherein: Pz is a pyrazolyl moiety and R, R' and R" are independently the same as or different from one another and each of R, R' and R" is independently selected from H, $C_6$–$C_{10}$ aryl, $C_6$–$C_{10}$ fluoroaryl, $C_1$–$C_6$ alkyl, $C_1$–$C_6$ fluoroalkyl, $C_1$–$C_6$ perfluoroalkyl, and $C_3$–$C_6$ cycloalkyl. The pyrazolate copper (I) Lewis base adducts of the invention include copper precursors of the formula (RR'R")PzCuL wherein: Pz is a pyrazolyl moiety and R, R' and R" are independently the same as or different from one another and each of R, R' and R" is independently selected from H, $C_6$–$C_{10}$ aryl, $C_6$–$C_{10}$ fluoroaryl, $C_1$–$C_6$ alkyl, $C_1$–$C_6$ fluoroalkyl, $C_1$–$C_6$ perfluoroalkyl, and $C_3$–$C_6$ cycloalkyl, with the proviso that at least one R contains fluorine; and L is a Lewis base ligand, for example a neutral Lewis base alkene, alkyne or diene, such as those deriving from compounds of the following formulae:

(I)
alkenes:

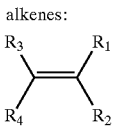

wherein $R_1$, $R_2$, $R_3$ or $R_4$ may be the same as or different from one another, and are independently selected from H, aryl, fluoroaryl, perfluoroaryl, $C_1$–$C_8$ alkyl or open-chain alkyl, $C_1$–$C_8$ fluoroalkyl, $C_1$–$C_8$ perfluoroalkyl, alkene, alkyne, ketones and cyclic versions of the aforementioned groups (II) alkynes of the formula:

wherein $R_1$ and $R_2$ may be the same or different and are independently selected from H, aryl, fluoroaryl, $C_1$–$C_8$, perfluoroaryl, $C_1$–$C_8$ alkyl, $C_1$–$C_8$ fluoroalkyl, $C_1$–$C_8$ perfluoroalkyl, vinyl, $C_5$–$C_6$ cycloalkyl, alkene, alkyne, ketone and cyclic versions of the aforementioned groups; and (III) dienes of the formula:

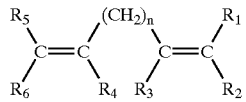

wherein $R_1$ $R_2$, $R_3$, $R_4$, $R_5$ and $R_6$ may be the same or different and are independently selected from H, and $C_1$–$C_3$ alkyl and wherein n=0, 1, 2, 3 or 4.

Pyrazolate copper (I) Lewis base adducts L of the invention may also be formed with amines as coordinated ligand species. Amine adducts may be formed for example by complexation of a pyrazolate copper (I) compound with an amine in a solvent composition comprising an amine solvent component. Preferred amine Lewis base ligand species L useful in the invention include primary, secondary and tertiary amines. More preferably, the amine Lewis base ligand species (L) may include triethylamine, tetramethylethylenediamine, tributylamine and tripropylamine.

Other useful Lewis base ligand species L include 1-hexene, vinyltrimethylsilane, 2-hexyne, 3-hexyne, 2-butyne, 5-vinyl-2-norbornene, 1,5-dimethylcyclooctadiene, 2-methyl-1-hexen-3-yne, 2,5-dimethyl-2,4-hexadiene, bis(trimethylsilyl)acetylene, dipentene, 1-pentene, 1-butene, 1-propene, isoprene, trimethylphosphine, triethylphosphine, dimethyl sulfide and diethyl sulfide.

Particularly preferred adduct species of the invention include pyrazolate copper (I) Lewis base adducts that are devoid of oxygen constituents therein.

More generally, the copper source reagent compounds and complexes of the invention may be of any suitable character consistent with the discussion herein. Illustrative copper precursors such as [(CF$_3$)$_2$PzCu]$_3$, (CF$_3$)$_2$PzCu(3-hexyne), and (CF$_3$)$_2$PzCu[bis(tms)acetylene], wherein Pz is a pyrazolyl moiety and tms is trimethylsilyl, e.g., (CH$_3$)$_3$Si—, are more fully described hereinafter, but it will be recognized that the present invention is broadly applicable to encompass a wide variety of fluorinated and non-fluorinated pyrazolate copper (I) complexes and their Lewis base adducts, as well as the use of such complexes and adducts in a wide variety of end uses involving the formation of copper for specific end uses and applications, including copper metallization of integrated circuitry and microelectronic device structures, formation of plating base seed layers, etc.

The invention also relates to a process for synthesizing the copper pyrazolate precursors, by reacting (RR'R")pyrazole with a stoichiometric excess of Cu$_2$O, preferably in a suitable solvent medium, such as an alkane, substituted alkanes, aryl, or substituted aryl solvent, and recovering (RR'R")pyrazolyl copper from the reaction volume, to provide a copper reagent that may itself be used in copper MOCVD, as well as being amenable to the formation of adducted species by reacting the (RR'R")pyrazolyl copper with a Lewis base compound, to yield a (RR'R")pyrazolyl copper Lewis base adduct. The adduct species are particularly useful in liquid delivery MOCVD processes to form copper, by delivering the composition to a process tool through use of a liquid delivery system. The adduct species may be delivered to the CVD process either neat or in solution. In some cases excess Lewis base ligand may be added to the solution composition or the Lewis base ligand may be used as the solvent.

The invention also relates to a process for synthesizing the copper pyrazolate precursors, by reacting bis(trifluoromethyl)pyrazole with a stoichiometric excess of $Cu_2O$, preferably in a suitable solvent medium, such as an alkane, haloalkane, aryl, or haloaryl solvent, and forming bis(trifluoromethyl)pyrazolyl copper from the reaction volume, to provide a copper reagent that may itself be used in copper MOCVD, as well as being amenable to the formation of adducted species by reacting the bis(trifluoromethyl)pyrazolyl copper with a Lewis base compound, to yield a bis(trifluoromethyl)pyrazolyl copper Lewis base adduct.

In CVD usage, the copper precursor of the invention is volatilized to form a precursor vapor that then is contacted with a substrate under elevated temperature vapor decomposition conditions to deposit copper on the substrate.

As a specific synthesis method, the copper pyrazolate compositions of the present invention are readily synthesized by reacting 3,5-bis(trifluoromethyl)pyrazole with an excess amount of $Cu_2O$ in a suitable solvent medium such as $CH_2Cl_2$ optionally in the presence of L (=neutral Lewis base ligand species), as shown in reaction equation 1 below, wherein Pz=pyrazolyl and wherein n is zero or 1.

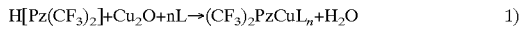

When n is zero, the synthesis is carried out in the absence of any L ligand species, to form $[(CF_3)_2PzCu]_3$ by reacting 3,5-bis(trifluoromethyl)pyrazole with an excess amount of $Cu_2O$ in the solvent, e.g., $CH_2Cl_2$ solvent.

Upon the completion of the reaction, the excess amount of $Cu_2O$ may be removed by filtration, e.g., by filtering the reaction mixture through Celite® or other filtration media, followed by removal of the solvent, e.g., under vacuum from the filtrate.

When no ligand L is present in the reaction mixture, $[(CF_3)_2PzCu]_3$ is obtained as a solid. Unlike $[(hfac)Cu]_n$, $[(CF_3)_2PzCu]_3$ is very stable, exhibiting no decomposition even up to 240° C. This affords direct purification of the copper complex prior to Lewis base adduct formation. By contrast the polymeric species of $[(hfac)Cu]_n$, undergoes a disproportionational reaction even at −50° C., forming Cu metal and $Cu(hfac)_2$.

$[(CF_3)_2PzCu]_3$ is volatile and thermally stable, and is usefully employed as a Cu MOCVD precursor under reducing ambient deposition conditions in the CVD reactor. The solid precursor can dissolve in organic solvents, and liquid delivery can be used to meter the solution into a vaporizer for transport to the reactor.

In the CVD reactor, in a hydrogen atmosphere, the reduction as expressed in equation 2 takes place to produce elemental copper, Cu(0).

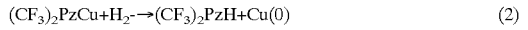

Figure 4:
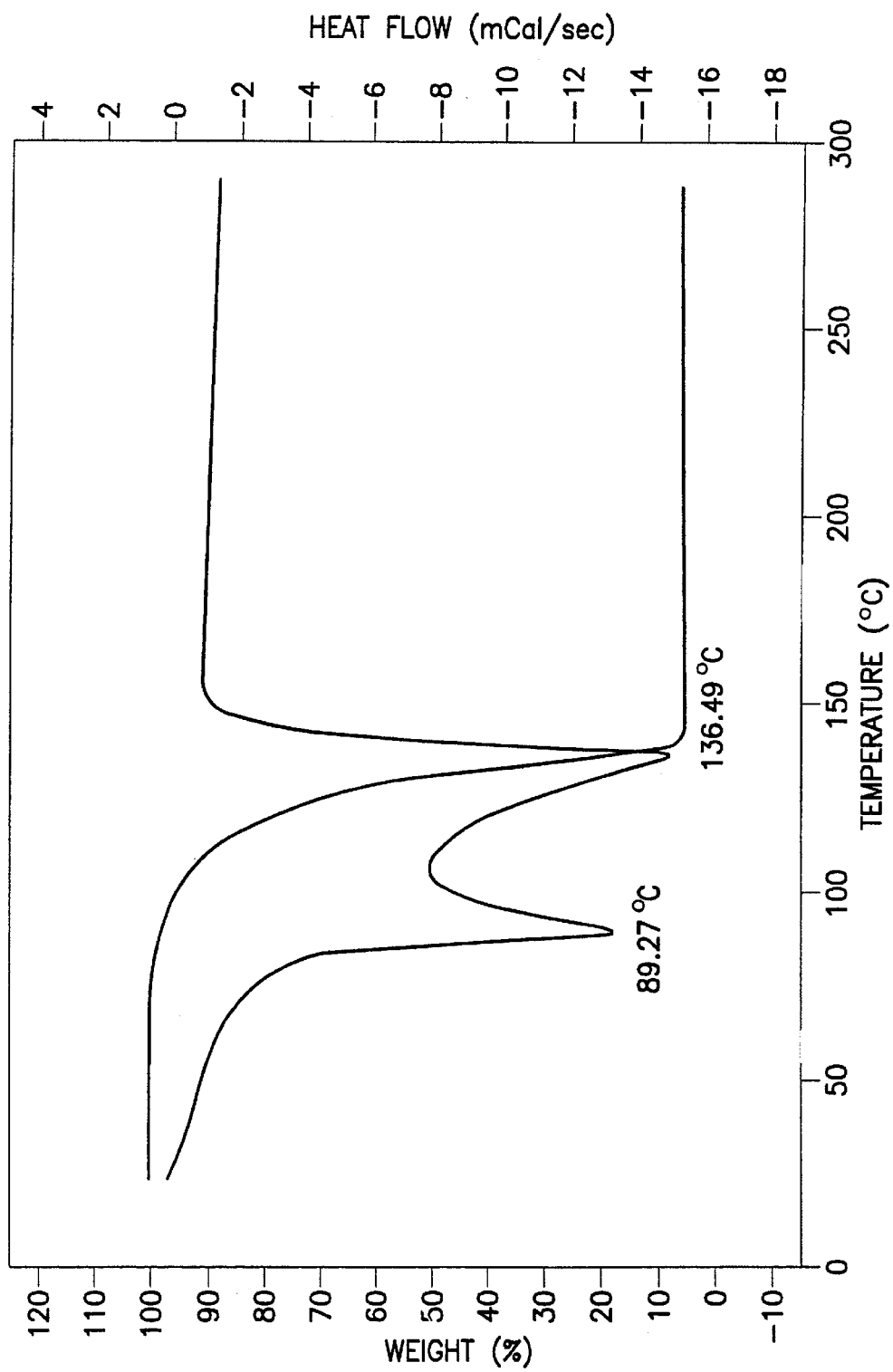
FIG. 4 is an STA thermal analysis plot for 3,5-bis (trifluoromethyl)pyrazole.

$(CF_3)_2PzH$ is the only by-product formed during the MOCVD process when $(CF_3)_2PzCu$ is used as a precursor. As a result of its volatility and stability, as depicted by FIG. 4, $(CF_3)_2PzH$ can be easily removed from the growing film and the CVD reactor.

Complexes of the formula $(CF_3)_2PzCu(L)$ are readily formed by carrying out the reaction of equation (1), involving reaction of 3,5-bis(trifluoromethyl)pyrazole with an excess amount of $Cu_2O$ in the solvent medium, together with the ligand species L in the reaction volume. The resultant adducted complexes exhibit increased solubility in organic solvents and are particularly useful in liquid delivery CVD processes.

The ligand species L may be any suitable neutral Lewis base species, e.g., alkene, alkyne, diene, ene-yne, ene-one, diyne, keto-ene, keto-yne or cyclic versions of the aforementioned species, etc. Specific examples of useful Lewis base species include 1-hexene, isoprene, vinyltrimethylsilane, 2-hexyne, 3-hexyne, 2-butyne, 5-vinyl-2-norbornene, 2,5-dimethyl-2,4-hexadiene, 1,5-dimethylcyclooctadiene, 2-methyl-1-hexen-3-yne, bis(trimethylsilyl)acetylene, 1-pentene, 1-butene, 1-propene and dipentene. Any suitable amines may also be used as a ligand species L.

The solvent medium used for the synthesis of $[(CF_3)_2PZCu]_3$ or Lewis base complexed adducts thereof may be any suitable solvent species or mixture of solvents appropriate to support the reaction. Examples of useful solvents include dichloromethane, trichloromethane, trichloroethane, butane, pentane, hexane, heptane, octane, toluene, dimethylformamide, and other alkane, aryl, amine and halocarbon solvents. In some cases the Lewis base ligand may be used as the solvent or as a constituent of the solvent mixture.

The present invention thus provides novel copper pyrazolate complexes using as copper MOCVD precursors. The copper pyrazolate complexes of the invention afford significant advantages over (hfac)CuL complexes, since they are non-oxygen containing, thermally stable, volatile and much less air-sensitive than prior art (hfac)CuL complexes.

The copper pyrazolate complexes of the invention may also be synthesized using corresponding non-halogenated or less-halogenated pyrazoles in place of 3,5-bis(trifluoromethyl)pyrazole for reaction with $Cu_2O$. Rather than the trifluoromethyl substituents on the pyrazole illustratively described hereinabove, corresponding pyrazole analogs may be employed with one or both of the trifluoromethyl substituents being alkyl or otherwise non-fluoro in character.

The invention therefore contemplates fluorinated and non-fluorinated pyrazolate copper (I) complexes and their Lewis base adducts for use as copper CVD precursors.

The invention correspondingly relates to a CVD process that uses these precursor materials, e.g., in the form of neat liquid precursors, as well as in solution compositions containing copper precursors of the invention in compatible solvent media, for copper metallization or the formation of copper seed layer via either liquid injection or direct vaporization.

More specifically, and by way of example, the copper pyrazolate precursor compositions of the present invention may be used during the formation of copper interconnect lines in semiconductor integrated circuitry, thin-film circuitry, thin-film packaging components and thin-film recording head coils. To form such integrated circuitry or thin-film circuitry, a semiconductor substrate may be utilized having a number of dielectric and conductive layers (multilayers) formed on and/or within the substrate. The semiconductor substrate may include a bare substrate or any number of constituent layers formed on a bare substrate.

In the broad practice of the present invention, a copper-containing layer may be formed on a semiconductor substrate using the copper pyrazolate precursor, for use in a first, second, third, or more metallization layer. Such copper layers typically are used in circuit locations requiring low resistivity, high performance and/or high speed circuit paths.

As discussed in the background section hereof, before a copper layer is formed on a semiconductor substrate, a barrier layer may be deposited or otherwise formed on the substrate.

Using the copper precursor compositions described herein, copper may then be deposited on the wafer using a CVD system. Metalorganic CVD (MOCVD) systems may be utilized for such purpose, such systems being well known in the semiconductor fabrication art. MOCVD systems potentially useful in the broad practice of the invention include atmospheric pressure MOCVD systems as well as low (or reduced) pressure MOCVD systems.

The precursor compositions of the present invention are not limited in respect of their use with such deposition tools, however, and other CVD tools, for example PECVD tools, or other deposition tools, may be utilized. Further, water, water-generating compounds, or other adjuvants to the precursor formulation may be mixed with the copper precursor upstream of, or within, the CVD tool. Similarly, reducing agents may be utilized in an analogous fashion.

As a further variation, when copper alloy compositions are to be deposited on the substrate, the copper precursor formulation may contain or be mixed with other metal source reagent materials, or such other reagent materials may be separately vaporized and introduced to the deposition chamber.

The compositions of the present invention may be delivered to a CVD reactor in a variety of ways. For example, a liquid delivery system may be utilized. Such systems generally include the use of liquid MFCs (mass flow controllers). An exemplary liquid delivery system useful in the general practice of the invention is the ADCS Sparta 150 Liquid Delivery System (commercially available from Advanced Technology Materials, Inc., Danbury, Conn.). A combined liquid delivery and flash vaporization process unit may be employed, such as the LDS300 liquid delivery and vaporizer unit (commercially available from Advanced Technology Materials, Inc., Danbury, Conn.), to enable low volatility materials to be volumetrically delivered, leading to reproducible transport and deposition without thermal decomposition of the precursor. Both of these considerations of reproducible transport and deposition without thermal decomposition are essential for providing a commercially acceptable copper CVD process.

Liquid delivery systems generally meter a desired volumetric quantity of a liquid or solution to achieve a uniform flow rate of the precursor composition to the CVD process tool. At the process tool chamber the liquid may be vaporized through use of a vaporizer or a transducer activated by ultrasound or acoustic techniques. Various configurations and types of liquid delivery systems are described in U.S. Pat. Nos. 5,204,314; 5,362,328; 5,536,323; and 5,711,816, the disclosures of which are hereby expressly incorporated herein by reference in their entireties.

In liquid delivery formulations, copper precursor complexes and adducts that are liquids may be used in neat liquid form, or liquid or solid copper complexes and adducts may be employed in solvent formulations containing same. Thus, copper precursor formulations of the invention may include solvent component(s) of suitable character as may be desirable and advantageous in a given end use application to form copper on a substrate. Suitable solvents may for example include alkane solvents, e.g., hexane, heptane, octane, pentane, or aryl solvents such as benzene or toluene, amines and amides, as well as other alkane, aryl and halocarbon solvents. The utility of specific solvent compositions for particular copper precursor complexes and adducts may be readily empirically determined, to select an appropriate single component or multiple component solvent medium for the liquid delivery vaporization and transport of the specific copper precursor employed. It is generally desirable to avoid oxo (—O—) solvents such as ethers as solvent species in the copper precursor formulations of the invention.

The use of the compositions disclosed herein is not limited to liquid delivery systems, and any method that adequately delivers the precursor composition to the process may be usefully employed. Thus, for example, bubbler-based delivery systems may be utilized. In such systems, an inert carrier gas may be bubbled through the precursor composition to provide a resulting gas, which is wholly or partially saturated with the vapor of the precursor composition, for flow to the CVD tool.

A wide variety of CVD process conditions may be utilized with the precursor compositions of the present invention. Generalized process conditions may include substrate temperature ranges of 150–400° C.; pressure ranges of 0.05–5 Torr; and carrier gas flows of helium, hydrogen, nitrogen, or argon at 25–750 sccm at a temperature approximately the same as the vaporizer.

The copper pyrazolate precursor compositions of the invention also have utility for the deposition of plating base layers, e.g., by liquid delivery CVD techniques, to achieve reproducible delivery, reproducible film growth and uniform deposition rates in the deposition of thin conductive films (e.g., having a thickness on the order of 1000 Angstroms).

The deposition of copper thin films with useful electrical properties (low resistivity) and good adhesion to the barrier layer (e.g., formed of TiN or TaN), are also achieved by the process and precursors of the present invention. The conformality of the deposited film is practically achievable only through CVD techniques that thereby provide a pathway to the achievement of "full-fill" copper metallization. The liquid delivery approach of the present invention, including "flash" vaporization and the use of copper precursor chemistry as herein disclosed, enable next-generation device geometries and dimensions to be attained, e.g., a conformal vertical interconnect of 0.13 micron linewidths with 4–8:1 aspect ratio. The conformal deposition of interconnects of these critical dimensions cannot be realized by currently available physical deposition methods. Thus, the approach of the present invention affords a viable pathway to future generation devices, and embodies a substantial advance in the art.

FIG. 1 is a schematic representation of a liquid delivery MOCVD system 100 that may be employed in the practice of the invention for metallization in the manufacture of semiconductor devices, or otherwise for forming a copper-containing material on a substrate, using a liquid source reagent.

The delivery system 100 includes a first fluid feed passage 10 into which a first fluid is introduced in the direction indicated by arrow $F_1$. The first fluid may comprise a carrier gas, such as argon, as well as other gaseous components, e.g., source compounds, additives, co-reactants, reducing agents or other species.

The first fluid feed passage 10 is connected to a gas distribution manifold at its proximal end 1, and is open at its distal end 13. The distal portion 16 of passage 10 is mounted in a housing 12 of a reactor, such as a CVD growth chamber. The distal portion 16 of the first fluid feed passage 10 thus is centrally disposed in the cylindrical portion 15 of the CVD reactor 12, to form an annular interior volume 17 therebetween.

Communicating with the annular interior volume 17 is a second fluid flow passage 18, into which second fluid is introduced in the direction indicated by arrow $F_2$, through the open end 19 of the passage. The second fluid introduced in passage 18 to the reactor may include other source reagent materials, or components or carrier gas species, such as hydrogen, nitrogen, argon, etc.

Disposed in the proximal portion 21 of the first fluid flow passage 10 is a flash vaporization matrix structure 26, which is joined in liquid delivery relationship by conduit 28 and conduit 32, having check valve 30 therebetween, to liquid reservoir 34. The liquid reservoir 34 may contain one or more copper pyrazolate precursors in accordance with the invention. If the particular copper pyrazolate precursor complex is of a solid form, the liquid reservoir 34 may be constructed and arranged to hold a solution comprising the copper pyrazolate precursor and a suitable solvent medium therefor, or if the copper pyrazolate precursor is a suitable liquid, then the reagent alone.

The copper pyrazolate precursor species if of solid form at ambient conditions is suitably dissolved or suspended in a compatible solvent medium, as more fully described in U.S. Pat. No. 5,820,664 issued Oct. 13, 1998 for "PRECURSOR COMPOSITIONS FOR CHEMICAL VAPOR DEPOSITION, AND LIGAND EXCHANGE RESISTANT METAL-ORGANIC PRECURSOR SOLUTIONS COMPRISING SAME," the disclosure of which is hereby incorporated herein in its entirety by reference.

Conduit 28 is sized and arranged (mounted on flash vaporization matrix structure 26) in such manner as to prevent premature evaporation of any volatile components (e.g., solvent constituents) of the source liquid that is flowed through conduit 28 to the vaporization matrix structure for flash vaporization thereon. The conduit 28 extends through lateral extension 20 of first fluid flow passage 10.

The delivery system 100 shown in FIG. 1 comprises a vaporization zone 22, which may be maintained at a suitable elevated temperature commensurate with the flash vaporization of reagent source liquid on the flash vaporization matrix structure 26. Downstream from the vaporization zone 22 is an injection zone 24, wherein a second fluid is introduced via second fluid flow passage 18. The injection zone 24 is maintained at a suitable temperature, which may be somewhat less than the temperature of the vaporization zone, depending on the various constituents introduced through the respective first and second fluid flow feed passages. In some instances of the present invention, it may be advantageous to introduce a copper precursor by injection via the injection zone.

In operation, the first fluid is flowed in the direction $F_1$ through first fluid flow passage into the reactor 12, being discharged at the distal open end 13 of the first fluid flow passage 10. Concurrently with such flow of gas therethrough, the reagent source liquid from reservoir 34 is flowed through conduit 32, check valve 30, and conduit 28, to the flash vaporization matrix structure 26.

The flash vaporization matrix structure 26 may be formed of any suitable material which does not deleteriously interact with the reagent source liquid or other fluid species introduced into the first fluid flow passage. The matrix structure should also be heatable to sufficient elevated temperature to effect flash vaporization of the reagent source liquid that is introduced from conduit 28 onto the surfaces of the matrix structure. The matrix structure may for example be formed of metals such as stainless steel, copper, silver, nickel, iridium, platinum, etc., as well as ceramics, high temperature glasses, quartz, chemically treated quartz, composite materials, and the like, the choice of a specific material of construction being dependent on the temperature regime which is encountered by the matrix structure, as well as the composition of the reagent source liquid and fluid flowed past the structure in the first fluid flow passage 10. Preferably, the matrix structure is constructed of an inert metal, and has a relatively high surface-to-volume ratio, as for example at least about 4, more preferably at least about 10, and most preferably at least about 100, when the surface and volume are measured in corresponding area and volume dimensional units (viz., square and cubic values of the same dimensional units). Preferably the matrix structure is foraminous (i.e., porous or perforate) in character.

The flash vaporization matrix structure may take the form of a screen, porous sintered material body, grid, or the like. The composition, surface area, and surface-to-volume characteristics of the matrix structure are selected so as to effect flash vaporization of the reagent source liquid on the surfaces of the structure, near contemporaneously with application of liquid thereon.

The conduit 28 introducing the reagent source liquid onto the matrix structure 26 may simply be an open-ended tube, i.e., a tube whose open end communicates with the matrix structure, whereby liquid issuing from the conduit flows onto the surfaces of the matrix structure for flash vaporization thereon, when the grid is heated to suitable elevated temperature. As previously discussed, conduit 28 is appropriately sized and arranged relative to the vaporization matrix structure 26 to prevent any undesirable premature evaporation of the reagent source liquid before the flash vaporization thereof on the matrix structure. In order to enhance the dispersion and distribution of reagent solution onto the surfaces of the matrix structure, the conduit 28 may have a restriction rod (not shown) centrally disposed therein to form an interior annular conduit, whereby pressure drop in the conduit is adjusted to a desired level, and whereby liquid appropriately issues in a thin film onto the matrix structure surfaces. Alternatively, the conduit 28 may be joined to a suitable nozzle or distributor means (not shown) at the distal end of the conduit, to facilitate distribution of source reagent liquid onto the matrix structure surfaces.

The source reagent solution reservoir 34 may be associated or otherwise coupled with a suitable liquid pumping means (not shown), such as a positive displacement liquid pump which effects discharge of reagent source liquid from the reservoir through conduit 32, check valve 30, and conduit 28 to the matrix structure 26. The reagent source liquid may be introduced onto the vaporization matrix structure in a steady stream injection mode or in a pulsed injection mode from the conduit 28. In general, steady stream injection of the reagent source liquid is desirable in CVD applications since it provides the most stable concentration of the source reagent in the downstream reactor, however, pulsed injection of the reagent source liquid may be advantageous in some applications.

Preferably, the matrix structure 26 is formed of a material of construction having a high specific heat capacity, so that the structure is substantially unaffected by heat of vaporization effects, whereby the matrix structure is suitably maintained at a desirable elevated temperature for continuous operation and vaporization of the reagent source liquid. Materials of construction which may contaminate the deposited films sought to be formed from the source reagent liquid, e.g., iron, should be avoided in the practice of the invention, in applications where the composition and stoichiometry of the deposited copper-containing film are critical.

The check valve 30 between conduits 28 and 32 controls the on/off flow of reagent source liquid therethrough to the matrix structure 26 and is required to prevent the uncontrolled delivery of the source reagent solution to the matrix structure 26 under reduced pressure operating conditions.

The reagent source liquid delivered to the heated matrix structure 26 is vaporized and then carried by a first fluid (carrier gas) into the deposition reaction chamber 12 for deposit of a copper-containing material on a substrate therein. The first fluid may also comprise other reagents from various upstream bubblers or other source means therefor.

Figure 2:
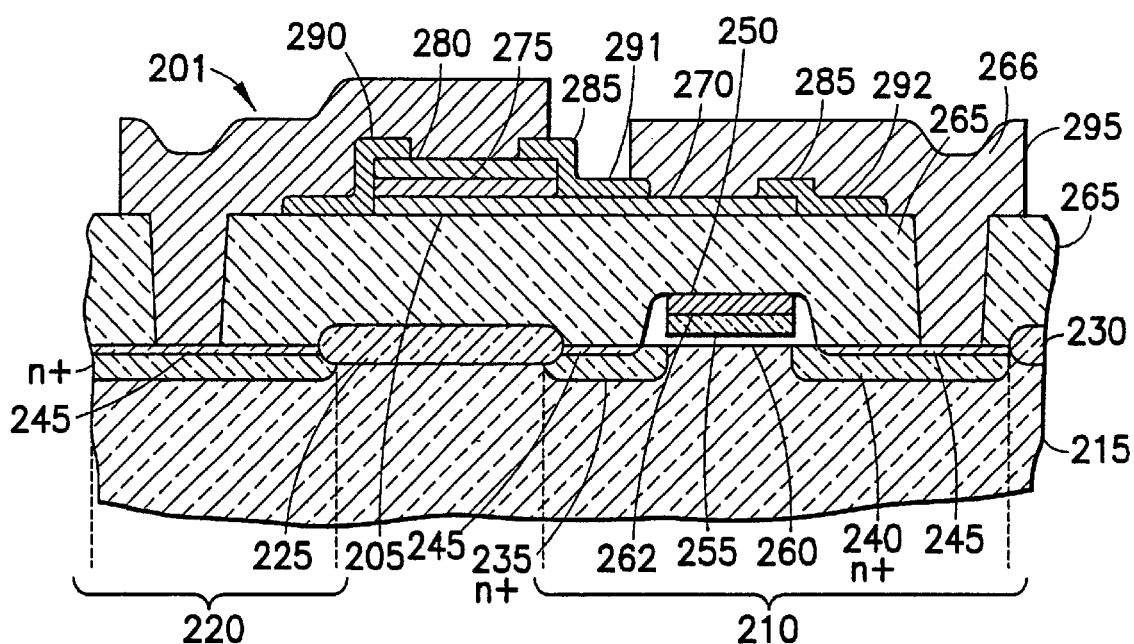
FIG. 2 schematically shows a portion of an exemplary IC with interconnects and an integral capacitor that may be fabricated in accordance with the invention.

FIG. 2 schematically shows a portion of an exemplary IC with an integral capacitor that may be fabricated in accordance with the invention. The illustrated portion of integrated circuit 201 includes a first active device 210, such as a conventional metal-oxide-semiconductor field effect transistor (MOSFET), and a capacitor 205 employing a dielectric film layer of (Ba,Sr) titanate formed on a substrate 215, such as a silicon substrate. A drain region of a second transistor 220 is also shown. The particular types of active devices employed, e.g., NMOS, PMOS or CMOS, are based on the desired operation of the integrated circuit and are not critical for practicing the present invention. Other suitable active devices include, for example, bipolar junction transistors and GaAs MESFETs.

The transistors 210 and 220 can be fabricated, for example, by conventional processing methods. In FIG. 2, the transistors 210 and 220 include field oxide regions 225 and 230 that are formed, for example, by $SiO_2$ and operate as insulators between the transistor 210 and adjacent devices, such as the transistor 220. Source and drain regions 235 and 240 of the transistor 210 are formed by doping with n-type impurities, such as arsenic or phosphorus for NMOS. An optional layer of silicide 245 is deposited over the source and drain regions 235 and 240 to reduce the source and drain resistance, which enables greater current delivery by the transistor 210.

A gate 250 of the transistor 210 includes, for example, polysilicon 255 doped with an n-type impurity, such as by an implant or vapor doping. The gate polysilicon 255 is disposed on a $SiO_2$ spacer 260. An optional layer of silicide 262 is also deposited over the gate polysilicon 255 to reduce the electrical resistance of the gate 250. An insulating layer 265 of, for example, P-glass which is an oxide doped with phosphorus, is then deposited on the transistors 210 and 220 to provide protection to the transistors 210 and 220 and to facilitate electrical connection. Contract windows 266 are then etched in the insulating layer 265 to expose the device gate 250 and source and drain regions, such as the regions 235 and 240. Although only the drain regions of the transistors 210 and 220 are exposed in the cross-section of the integrated circuit illustrated in FIG. 2, it should be readily understood that the gate and source are exposed at other areas of the integrated circuit 1 that are outside the illustrated cross-section.

The capacitor 205 includes a first electrode 270 formed on the insulating layer surface, a dielectric thin film region 275 on the first electrode 270, and a second electrode 280 formed on the dielectric film region 275 opposite the first electrode 270. It is possible for the first electrode 270 to have a two-layer structure. Such a structure is, for example, a layer of platinum formed over a layer of Ti-nitride or TiAlN. Platinum alone is not a suitable electrode material, however, since it adversely chemically reacts with silicon. As a consequence, a diffusion barrier is advantageously employed as the second electrode layer which is in contact with the insulating layer surface, to substantially prevent a chemical reaction between the platinum and the silicon of the substrate 215. Suitable thicknesses for each layer of the two-layer structure are in the range of 0.01 to 0.5 $\mu m$.

It is further possible for the first electrode 270 to be a single layer structure of an appropriate conductive material. Overall suitable thicknesses for the first electrode 270, whether a one or two layer structure, are in the range of approximately 0.1 to 0.5 $\mu m$. Thicknesses less than 0.1 $\mu m$ are undesirable because of its high electrical resistance while thicknesses greater than 0.5 $\mu m$ are generally disadvantageous because of high fabrication cost and poor adherence. The first electrode 270 is larger than the second electrode 280 to provide electrical connection to the first electrode 270.

After formation of the capacitor 205, an insulating material 285, such as, for example, $SiO_2$ is deposited on edge regions 290, 291 and 292 of the capacitor 205 to prevent short circuits between the first and second capacitor electrodes 270 and 280 when the interconnection layer is formed. A copper interconnection layer 295 is then formed on the insulation layer and corresponding etched contact windows to electrically connect the devices 210 and 220 and the capacitor 205, by CVD using a copper precursor in accordance with the present invention. In the integrated circuit 201, the drain 240 of the transistor 210 is electrically connected to the first electrode 270 of the capacitor 280 and the capacitor's second electrode 280 is electrically connected to the source of the transistor 220.

The features and advantages of the invention are more fully apparent from the following non-limiting examples.

EXAMPLE 1

Figure 3:
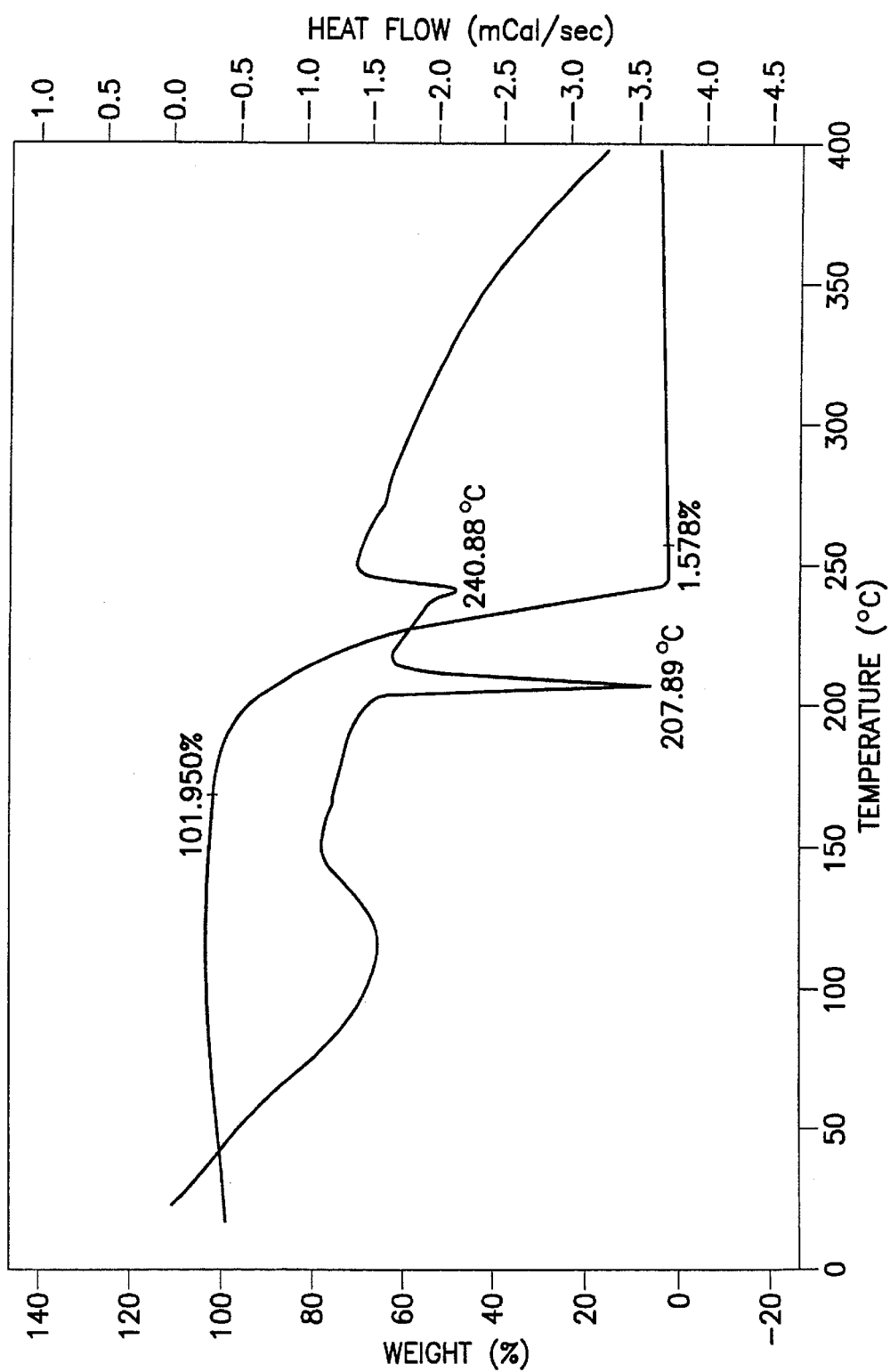
FIG. 3 is an STA thermal analysis plot for $[(CF_3)_2PzCu]_3$.

$[(CF_3)_2PzCu]_3$ was synthesized by reacting 3,5-bis (trifluoromethyl)pyrazole with an excess amount of $Cu_2O$ in $CH_2Cl_2$ solvent. Upon the completion of the reaction, the excess amount of $Cu_2O$ was filtered through Celite®. Removal of the solvent under vacuo from the filtrate gave a white solid. An STA thermal analysis plot for $[(CF_3)_2PzCu]_3$ is shown in FIG. 3 and evidences a melting endotherm peak at 208° C. and complete transport below 240° C. without significant decomposition (residue).

EXAMPLE 2

An STA thermal analysis was conducted for $(CF_3)_2PzH$ to determine the properties of such by-product of copper MOCVD when $[(CF_3)_2PzCu]_3$ is used as a precursor and the CVD process is conducted under reducing conditions using a hydrogen atmosphere.

The corresponding STA thermal analysis plot for $(CF_3)_2PzH$ is shown in FIG. 4 and shows that the onset of transport begins at 90° C., and was completed below 140° C. at atmospheric pressure.

EXAMPLE 3

Figure 5:
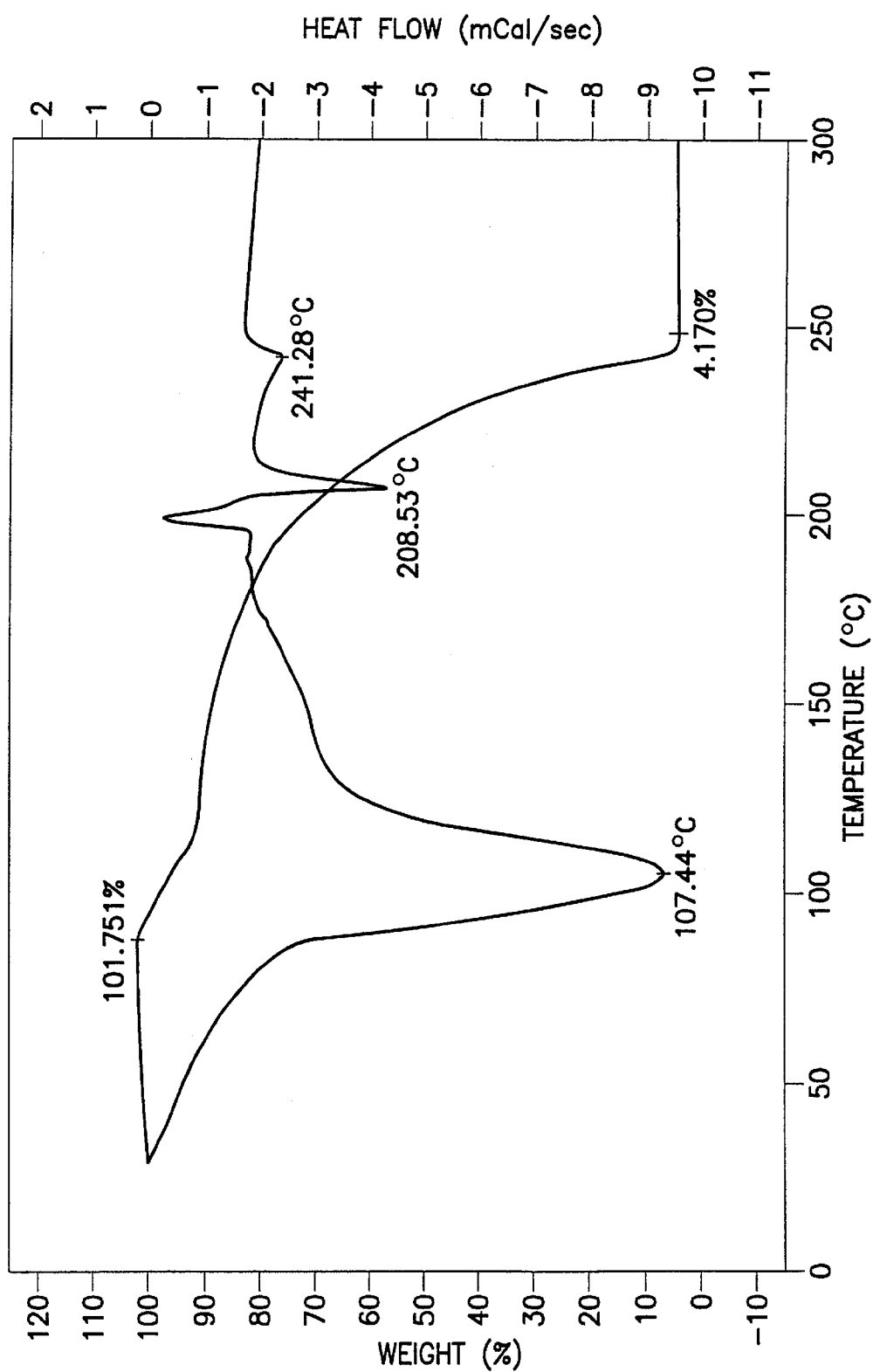
FIG. 5 is an STA thermal analysis plot for $(CF_3)_2PzCu$ (3-hexyne).

$(CF_3)_2PzCu(3\text{-hexyne})$ was synthesized by reacting $(CF_3)_2PzH$ with an excess amount of $Cu_2O$ in the presence of 3-hexyne in $CH_2Cl_2$. After the reaction was completed, the mixture was filtered, and a colorless filtrate was obtained. Removal of volatiles under vacuum gave white solid product. $^1H$ NMR study revealed that it was $(CF_3)_2PzCu(3\text{-hexyne})$. Thermal analysis (see the FIG. 5 STA thermal analysis plot) indicated the compound lost the alkyne Lewis base ligand around 110° C. After the dissociation of the alkyne ligand, a melting endotherm appeared at 208° C., indicative of the formation of the trimeric $[(CF_3)_2PzCu]_3$ that transports intact below 240° C.

EXAMPLE 4

Figure 6:
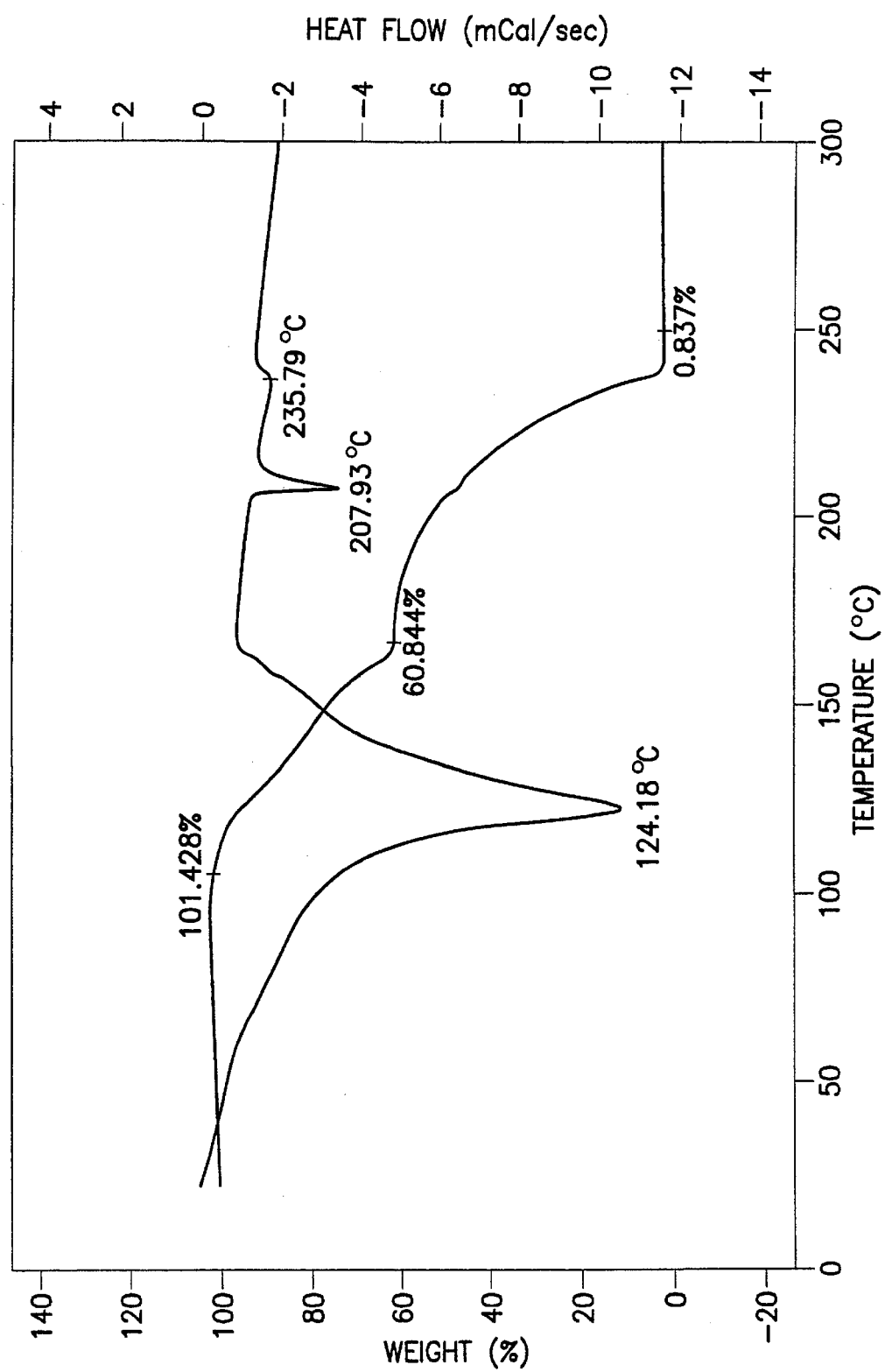
FIG. 6 is an STA thermal analysis plot for $(CF_3)_2PzCu$ [bis(tms)acetylene].

[(CF$_3$)$_2$PzCu]$_3$ was mixed with bis(tms)acetylene in CH$_2$Cl$_2$. After 5 hours, removal of volatiles gave an off-white solid. The solid was further purified by recrystallization in n-pentane. Pale yellow crystals were obtained. $^1$H NMR study revealed that this compound was (CF$_3$)$_2$PzCu[bis(tms)acetylene]. Thermal analysis, shown in the FIG. 6 STA thermal analysis plot, revealed that the compound lost the alkyne ligand around 124° C., forming a material with a melting point at 208° C., indicative of the formation of trimeric [(CF$_3$)$_2$PzCu]$_3$. This Lewis base ligand does not prevent liquid delivery and efficient vaporization.

Figure 7:
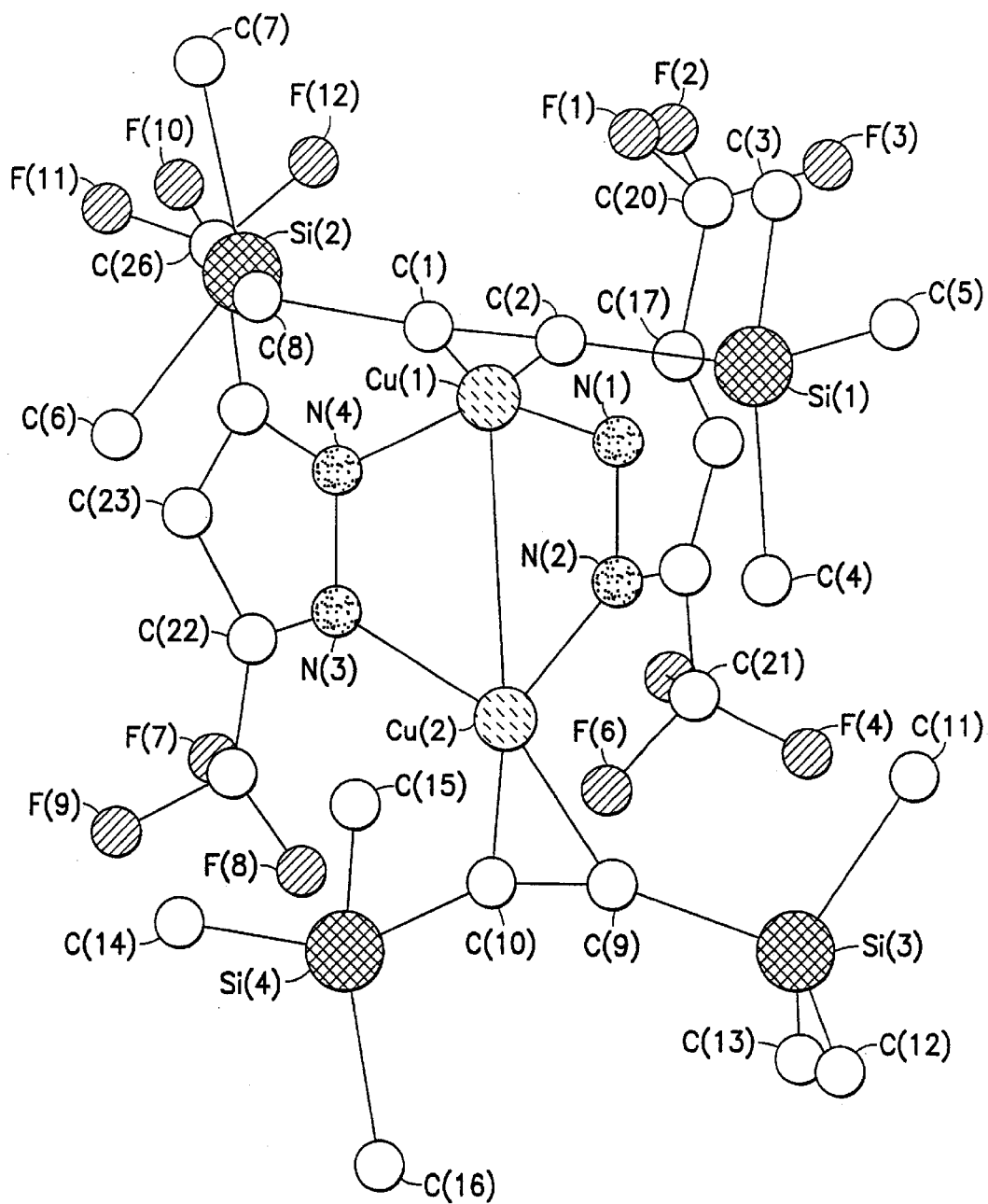
FIG. 7 is an Ortep representation of 3,5-$(CF_3)_2PzCu$[bis (tms)acetylene].

Single crystal X-ray diffraction studies revealed that (CF$_3$)$_2$PzCu[bis(tms)acetylene] was a dimer, having the formula reflected in the FIG. 7 Ortep representation of the molecular structure.

While the invention has been described herein with reference to specific features and illustrative embodiments, it will be recognized that the utility of the invention is not thus limited, but rather extends to and encompasses other features, modifications and alternative embodiments as will readily suggest themselves to those of ordinary skill in the art based on the disclosure and illustrative teachings herein. The claims that follow are therefore to be construed and interpreted as including all such features, modifications and alternative embodiments within their spirit and scope.

What is claimed is:

1. A copper precursor formulation, comprising:
   a precursor composition selected from the group consisting of:
      pyrazolate copper (I) compounds of the formula [(RR'R")PzCu]$_3$ wherein: Pz is a pyrazolyl moiety and R, R' and R" are independently the same as or different from one another and each of R, R' and R" is independently selected from the group consisting of H, C$_6$–C$_{10}$ aryl, C$_6$–C$_{10}$ fluoroaryl, C$_1$–C$_6$ alkyl, C$_1$–C$_6$ fluoroalkyl, C$_1$–C$_6$ perfluoroalkyl, C$_6$–C$_{10}$ perfluoroaryl and C$_3$–C$_6$ cycloalkyl, with the proviso that at least one R contains fluorine; and
      pyrazolate copper (I) Lewis base adducts of the formula (RR'R")PzCuL wherein:
         Pz is a pyrazolyl moiety and R, R' and R" are independently the same as or different from one another and each of R, R' and R" is independently selected from the group consisting of H, C$_6$–C$_{10}$ aryl, C$_6$–C$_{10}$ fluoroaryl, C$_1$–C$_6$ alkyl, C$_1$–C$_6$ fluoroalkyl, C$_1$–C$_6$ perfluoroalkyl, C$_6$–C$_{10}$ perfluoroaryl and C$_3$–C$_6$ cycloalkyl, with the proviso that at least one R contains fluorine; and L is a Lewis base ligand; and
   a solvent composition for the precursor composition.

2. A copper precursor formulation according to claim 1, wherein said solvent composition comprises an organic solvent.

3. A copper precursor formulation according to claim 1, wherein said solvent composition comprises a solvent selected from the group consisting of alkane, aryl, amine and halocarbon solvents.

4. The copper precursor formulation according to claim 3, wherein said solvent composition further comprises a neutral Lewis-base ligand.

5. The copper precursor formulation according to claim 4, wherein said neutral Lewis base ligand of the solvent composition and said Lewis-base adduct of the precursor composition are the same.

6. The copper precursor formulation according to claim 1, wherein the solvent composition comprises a neutral Lewis-base ligand.

7. A copper precursor formulation according to claim 1, wherein said solvent composition comprises a solvent selected from the group consisting of hexane, heptane, octane, pentane, dichloromethane, trichloromethane, trichloroethane, benzene, toluene, and dimethylformamide.

8. A copper precursor formulation according to claim 1, wherein said solvent composition is substantially free of oxo (—O—) solvents.

9. A copper precursor formulation useful for liquid delivery metalorganic chemical vapor deposition of copper, comprising:
   a precursor composition selected from the group consisting of:
      [(RR'R")PzCu]$_3$ wherein: Pz is a pyrazolyl moiety and R, R' and R" are independently the same as or different from one another and each of R, R' and R" is independently selected from the group consisting of H, C$_6$–C$_{10}$ aryl, C$_6$–C$_{10}$ fluoroaryl, C$_1$–C$_6$ alkyl, C$_1$–C$_6$ fluoroalkyl, C$_1$–C$_6$ perfluoroalkyl, and C$_3$–C$_6$ cycloalkyl; and pyrazolate copper (I) Lewis base adducts; and
      (RR'R")PzCuL wherein: Pz is a pyrazolyl moiety and R, R' and R" are independently the same as or different from one another and each of R, R' and R" is independently selected from the group consisting of H, C$_6$–C$_{10}$ aryl, C$_6$–C$_{10}$ fluoroaryl, C$_1$–C$_6$ alkyl, C$_1$–C$_6$ fluoroalkyl, C$_1$–C$_6$ perfluoroalkyl, and C$_3$–C$_6$ cycloalkyl, with the proviso that at least one R contains fluorine; and L is a neutral Lewis base ligand; and
   a solvent composition for the precursor composition.

* * * * *